United States Patent
Michelsson et al.

(10) Patent No.: US 7,657,077 B2
(45) Date of Patent: Feb. 2, 2010

(54) DETECTING DEFECTS BY THREE-WAY DIE-TO-DIE COMPARISON WITH FALSE MAJORITY DETERMINATION

(75) Inventors: Detlef Michelsson, Wetzlar-Naunheim (DE); Steffen Gerlach, Giessen (DE); Bernd Jungmann, Marburg (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 681 days.

(21) Appl. No.: 11/364,103

(22) Filed: Feb. 28, 2006

(65) Prior Publication Data

US 2006/0204109 A1   Sep. 14, 2006

(30) Foreign Application Priority Data

Mar. 11, 2005   (DE) .................. 10 2005 011 237

(51) Int. Cl.
*G06K 9/00* (2006.01)
*H01L 21/66* (2006.01)
*G01N 21/00* (2006.01)

(52) U.S. Cl. .................. 382/144; 382/149; 438/16; 356/237.5

(58) Field of Classification Search ............. 382/144, 382/145, 147, 149, 151, 219, 318; 438/16; 348/87, 126; 356/237.1, 237.2, 237.3, 237.4, 356/237.5
See application file for complete search history.

(56) References Cited

U.S. PATENT DOCUMENTS

| | | | |
|---|---|---|---|
| 4,165,764 A | 8/1979 | Grandclement | |
| 5,002,022 A | 3/1991 | Perr | |
| 6,493,645 B1 | 12/2002 | Hladschik | |
| 6,512,843 B1* | 1/2003 | Kuwabara | 382/149 |
| 6,973,208 B2* | 12/2005 | Kuwabara | 382/145 |
| 2001/0036306 A1 | 11/2001 | Wienecke | |
| 2002/0094120 A1* | 7/2002 | Hiroi et al. | 382/149 |
| 2004/0047501 A1 | 3/2004 | Kuwabara | |
| 2004/0165764 A1* | 8/2004 | Michelsson | 382/147 |
| 2004/0264760 A1* | 12/2004 | Ishikawa | 382/145 |

FOREIGN PATENT DOCUMENTS

| | | |
|---|---|---|
| DE | 100 11 200 A1 | 9/2001 |
| DE | 101 01 203 A1 | 9/2001 |
| DE | 100 27 135 A1 | 12/2001 |
| DE | 103 07 358 B3 | 7/2004 |
| DE | 103 07 373 A1 | 9/2004 |

* cited by examiner

*Primary Examiner*—Bhavesh M Mehta
*Assistant Examiner*—Barry Drennan
(74) *Attorney, Agent, or Firm*—Houston Eliseeva LLP

(57) ABSTRACT

A method of determining defects in a plurality of images having essentially the same image contents is disclosed. A comparison operation is carried out once three fully comparable images having essentially the same image contents are present in the intermediate memory. The stored individual images are accessed randomly. A paired comparison operation between the three difference images is carried out.

5 Claims, 8 Drawing Sheets

State of the Art

US 7,657,077 B2

DETECTING DEFECTS BY THREE-WAY DIE-TO-DIE COMPARISON WITH FALSE MAJORITY DETERMINATION

RELATED APPLICATIONS

This application claims priority to German application serial number DE 10 2005 011 237.4 filed on Mar. 11, 2005, which is incorporated herein by reference in its entirety.

FIELD OF THE INVENTION

The present invention relates to a method of detecting defects in images wherein a plurality of individual images are recorded which constitute partial images of the surface of a disk-like object.

BACKGROUND OF THE INVENTION

In semiconductor manufacture, during the manufacturing process, wafers are sequentially processed in a plurality of process steps, wherein a plurality of similar, repetitive structural elements, the so-called dies, are produced on a wafer. As integration densities increase, the requirements as to the quality of the structures formed on the wafer become ever more demanding. To be able to verify the quality of the structures formed and to find defects, if any, the requirements as to the quality, the precision and the reproducibility of the components and process steps for handling the wafer are correspondingly stringent. This means that in the production of a wafer comprising a great number of process steps and with the great number of layers of photoresist or the like to be applied, the reliable and early detection of defects in the individual structures or structural elements is particularly important.

German patent application DE 103 07 358 discloses a method and apparatus for scanning a semiconductor wafer. On-the-fly images of areas on the wafer are taken by a camera. When the scanning line is changed, a continuously curved translation path is created by at least partially superimposing the relative movement between the wafer and the camera in the direction of the scanning line and normal to it. This serves to save time and to increase wafer throughput.

German patent application DE 103 07 373 discloses that depending on the size of the stepper and die (design) the size of the SAW varies greatly. Generally it cannot be expected that a SAW can be recorded with a single camera image. A SAW is therefore subdivided into portions (segments) of equal size. Each logical SAW segment is associated with a SAW index. The images of the individual SAW segments are stored in a memory and can be retrieved from there by making reference to the index.

US Patent Application. US 2004/0047501 discloses a visual inspection device and method. The chips on the wafer are arranged in lines and subdivided into groups. The images of the chips of a group are compared with each other. If a group contains three chips, this means that the first chip is compared with the third chip, the first chip is compared with the second chip, and the second chip is compared with the third chip. In parallel to this, images are continued to be obtained. The analysis of the images is limited to an analysis of the images of one scanning line. Moreover, the detection of defects in the edge area of a wafer is not possible.

SUMMARY OF THE INVENTION

It is therefore an object of the present invention to provide a method enabling defects to be detected as early and as reliably as possible irrespective of their position on the disk-like object.

The selection of the images for comparison, in devices working on the principles of the prior art, is usually determined by the order in which the images to be compared are recorded. Usually the images are obtained in a meandering scanning process, if by means of a line scanning camera with continuous lighting, by means of array cameras or with flash lighting. The simplest form of a selection of the images to be compared is therefore the selection of each next or second next neighbor in the scanning direction. However, this leads to a number of problems when the recorded images are evaluated. When edge sections are to be analyzed, each edge section image does not constitute a fully comparable partner for the images from the inner areas of the wafer. In edge section images, only part of the image area is covered with structured elements. Further, it is also possible that with some wafer designs, individual contact or test surfaces are provided which have a different image content from the rest of the wafer. These areas must be excluded from the comparison process. Images with portions of these exclusion areas are also not fully comparable partners to images from the inner areas of the wafer. It is also particularly disadvantageous if a comparison of the images is limited to a single scanning line. Situations can arise where a whole scanning line only consists of edge section images, or where the number of comparable images is reduced to below three by the presence of exclusion areas. Further, in wafer manufacture, a phenomenon can arise wherein the recorded wafer images are partially incompatible with the principle that areas have to have the same appearance. A different hue of color may be overlapping in the inner areas of the wafer than near the edge. It is desirable to find comparable partners having a basic color hue which is as similar as possible. This can usually be found near the original image, however, not necessarily in the same scanning line. Frequently the criterion of the same distance to the wafer center is better suited as a selection criterion.

According to the present invention this object is achieved by a method of inspecting a wafer comprising the steps of:

recording a plurality of individual images of a surface of a disk-like object;

storing the individual images in an intermediate memory;

carrying out a comparison operation once three fully comparable images having essentially the same image contents are present in the intermediate memory, wherein the stored individual images are randomly accessed and wherein the recording operation of the individual images is carried out in parallel to the comparison operation; in that a first difference is formed of the first and second recorded individual images, a second difference is formed of the second and third recorded individual images and a third difference is formed of the third and first recorded individual images, and in that by means of a comparison between the third difference and the first difference, by means of a comparison between the first difference and the second difference and by means of a comparison between the second difference and the third difference the presence of a defect in the recorded individual images is determined.

The method of determining defects in a plurality of images having essentially the same image content is advantageous in that first a plurality of individual images are recorded from a surface of a disk-like object. These recorded individual images are stored in an intermediate memory. Parallel to this, a comparison operation can be carried out if three fully comparable images having essentially the same image content are present in the intermediate memory, wherein the access to the stored individual images is random and wherein the recording of the individual images is carried out in parallel to the comparison operation. According to the comparison operation, a first difference is formed of the first and the second recorded individual image, a second difference of the second and the third recorded individual image and a third difference of the third and the first recorded individual image. Finally, the differences are compared with each other, and the difference between the individual differences is determined. Thus the presence of a defect in the recorded individual images is detected by means of a comparison between the third difference and the first difference, by means of a comparison between the first difference and the second difference, and by means of a comparison between the second difference and the third difference.

The random access to the recorded individual images also facilitates the analysis of edge section images and of exclusion zones on the disk-like object. For analyzing the individual images of edge section images and exclusion zones, partner images are relied upon which have already been or are still to be analyzed in other groups of three.

The comparison operation between the three recorded individual images is not limited to the recorded individual images of a single scanning line.

To create an alignment of the three recorded individual images, first the present displacement of the three recorded individual images to each other is determined with subpixel accuracy. For each recorded individual image an optimal displacement to be carried out is calculated which would lead to the three recorded individual images to be compared eventually having their image contents take up the same position within their images with subpixel accuracy.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention.

Other advantages and advantageous embodiments of the present invention will be described in the following with reference to the accompanying drawings, in which.

DETAILED DESCRIPTION OF THE PREFERRED EMBODIMENTS

Figure 1:
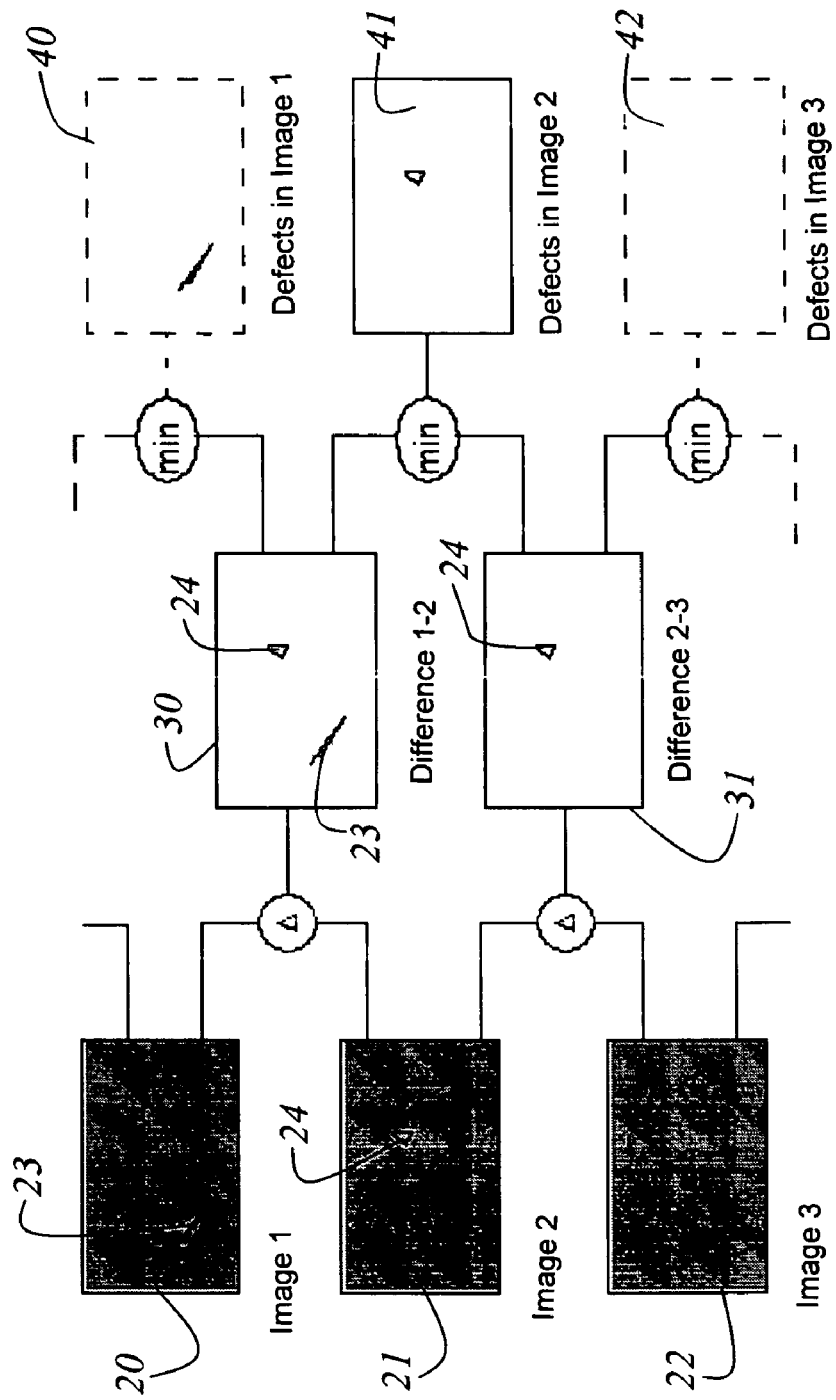
FIG. 1 is a schematic view of the method for determining defects in various image contents according to the present invention.

FIG. 1 shows a method for the detection of defects according to the prior art. The first image 20, the second image 21, the third image 22 are taken at different locations of the disk-like object (wafer), in which the same image information is to be expected. In the first image 20 a first defect 23 is in the form of a scratch. In the second image 21 a second defect 24 is in the form of a triangular scratch. The third image 24 is free of defects. A first difference 30 is formed of the first image 20 and the second image 21. Further, a second difference 31 is formed of the second image 21 and the third image 22. In difference images 30 and 31, the repetitive structure of the individual images 20, 21, and 22 is no longer visible. Difference images 30 and 31 only show the deviations in the images. In the first difference image 30, the first defect 23 is visible together with the second defect 24. In the second difference image 31, only the second defect 24 is visible, since no defect was present in the third image 22. Finally, two consecutive difference images, here difference image 30 and difference image 31, are compared with each other in order to find common features in the two difference images. From this comparison, the defects can be assigned to the correct recorded individual images 20 to 22. A significant difference could only be found in the second defect image 41, which was derived from the comparison of the first difference image 30 and the second difference image 31, which is a defect and is to be assigned to the second image 21. On the basis of the comparison no unequivocal decision could be made as to the presence of a defect in the first comparison image 40 and the third comparison image 42.

Figure 2:
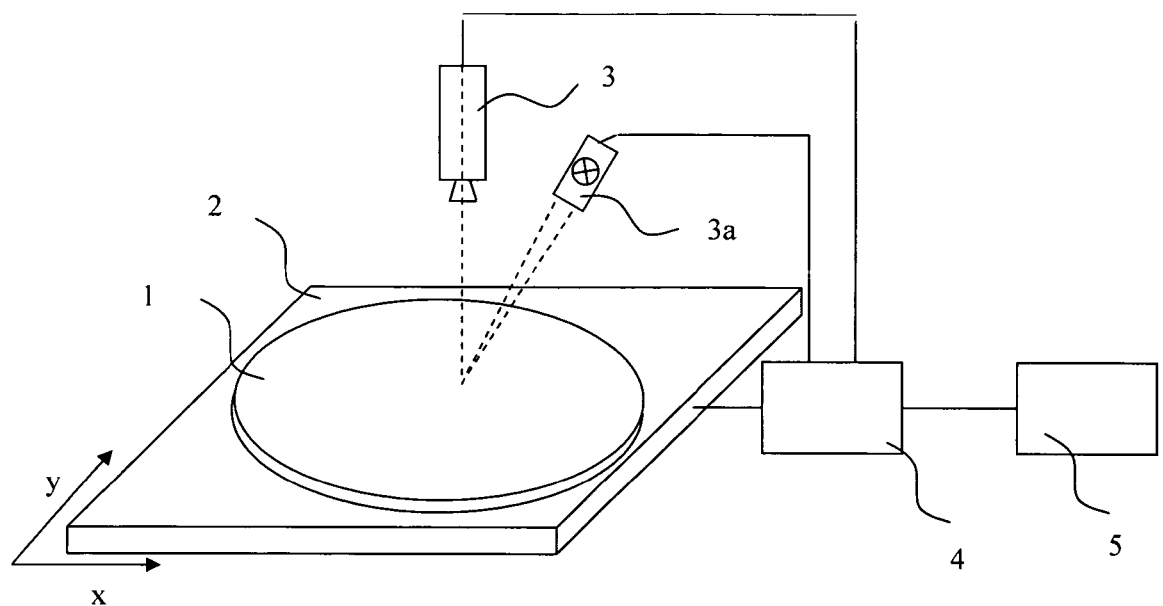
FIG. 2 is an arrangement of a camera table with a wafer and a scanner device for recording individual images from the surface of the wafer.

FIG. 2 schematically shows a disk-like object 1 (wafer) to be scanned, which is supported on a scanning table 2. A plurality of images is taken of disk-like object 1 by means of a camera 3. In order to create a relative movement between the scanning table and the camera, an x-y scanning table is used which can be traversed along the coordinate axis directions x and y. Unlike the scanning table, the camera is fixedly installed.

To be able to carry out a great number of image recordings with the camera 3, the scanning table 2 is continuously traversed below camera 3 at constant speed. The desired images of selected areas or of the complete surface of disk-like object 1 are thus recorded in an on-the-fly process. A control unit 4 determines the movement and the speed of the scanning table and also controls the camera. This coordinated control of the scanning table and the camera enables images to be taken of the desired areas of disk-like object 1.

Due to the on-the-fly imaging, depending on the speed of scanning table 2, correspondingly short exposure times are necessary for the individual images, so that smeared images are avoided. Short exposure times mean that disk-like object 1 has to be lighted with very high light intensities. A high lighting density can also be achieved by having a lighting means 3a focus its light only onto such area of disk-like object 1 that is necessary for the image recording of the camera. The recorded images are evaluated directly after taking the image or corresponding to the presence of a certain number of comparable recorded images by a fast algorithm. It is thus necessary for various images to be intermediately stored, so that the evaluation can also be carried out during the image recording process.

Figure 3:
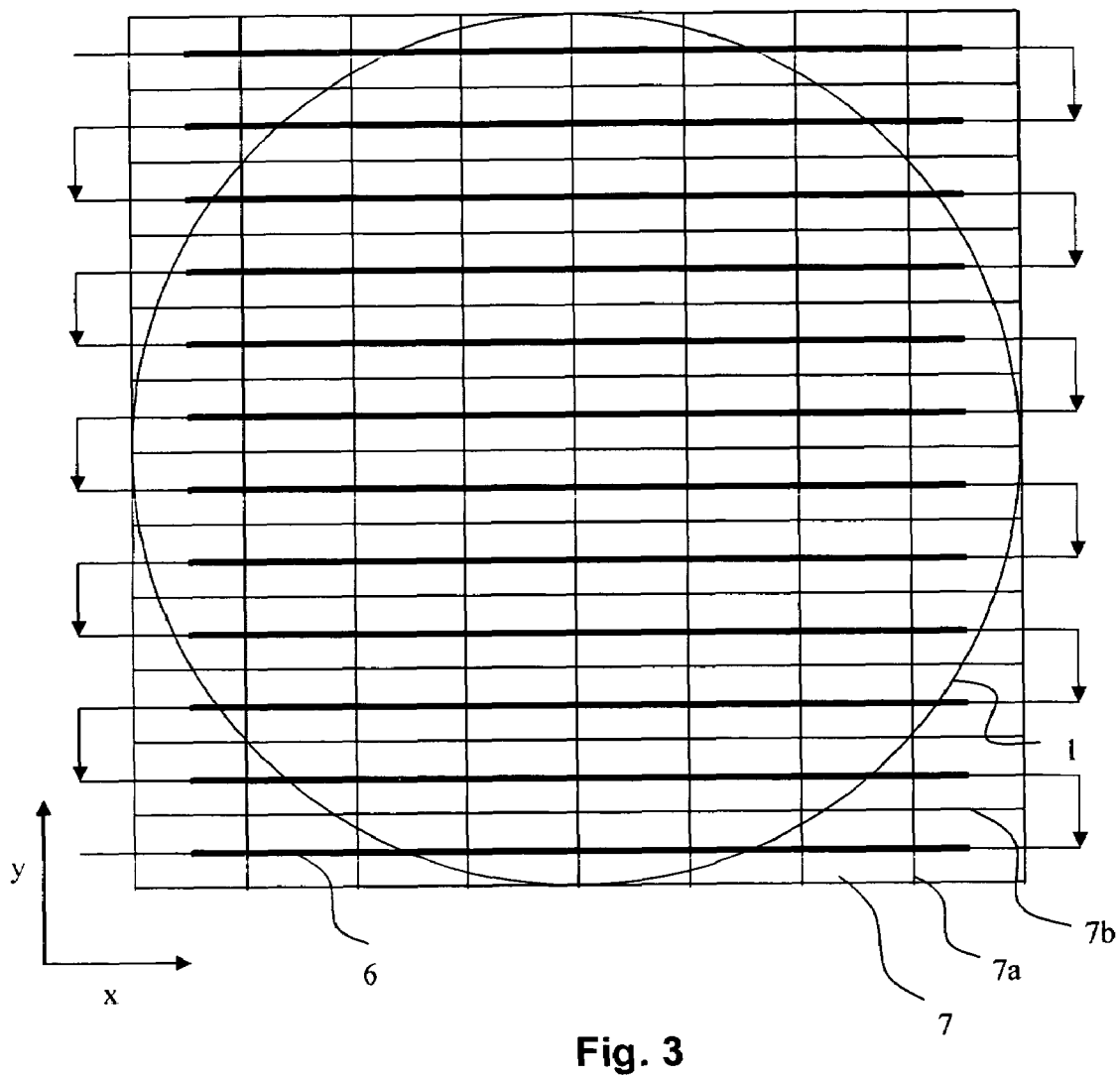
FIG. 3 is a schematic view of the scanning path across the surface of the disk-like object (wafer) which serves to take a plurality of individual images from the surface of the disk-like object.

In FIG. 3 one possibility of a scanning path 6 for a scanning sequence is shown wherein disk-like object 1 is scanned in full. Images are taken of the whole surface of disk-like object 1 for a 100% inspection. Disk-like object 1 is scanned on a line-by-line basis in such a way that the rectangle sides 7a, 7b of neighboring image areas each corresponding to the image field 7 of camera 3 are at least adjacent. The scanning lines are of equal length and cover disk-like object 1 in its diameter. The scanning lines thus begin and end at a predetermined x coordinate outside of the wafer.

Figure 4:
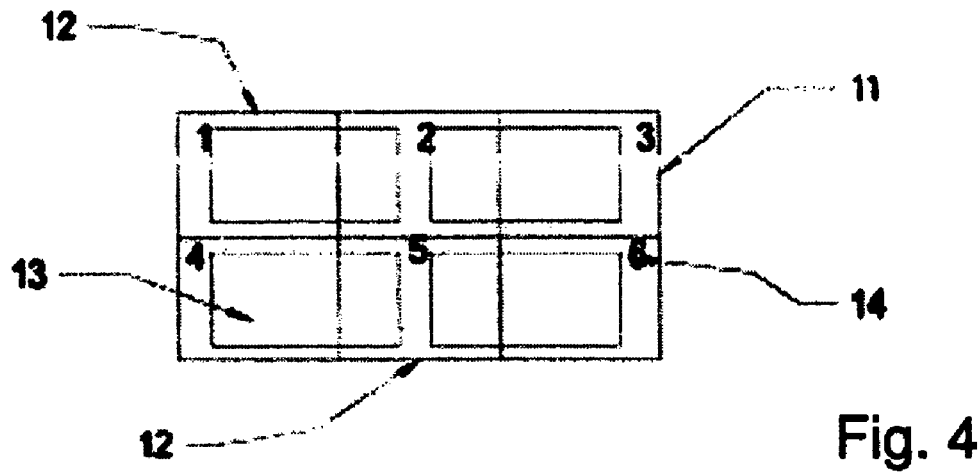
FIG. 4 shows a logically segmented SAW with corresponding index numbers.

FIG. 4 shows a logically segmented SAW 11 subdivided into segments 12. The SAW 11 in turn comprises a plurality of dies 13. The individual segments 12 are designated with a serial index 14. In the present case, this index reaches number 6.

Figure 5:
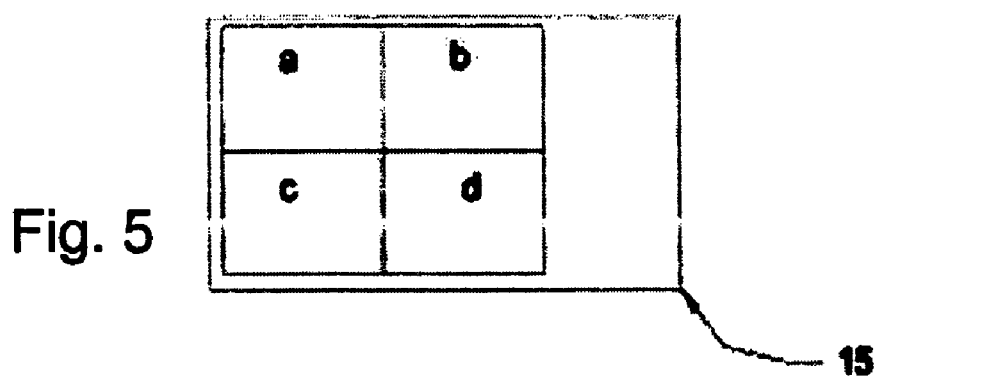
FIG. 5 shows an image array of a camera with index characters of logical SAW elements able to be imaged.

FIG. 5 shows an image section 15 comprising four image field segments designated with the characters a to d. These characters are also a corresponding index.

Figure 6:
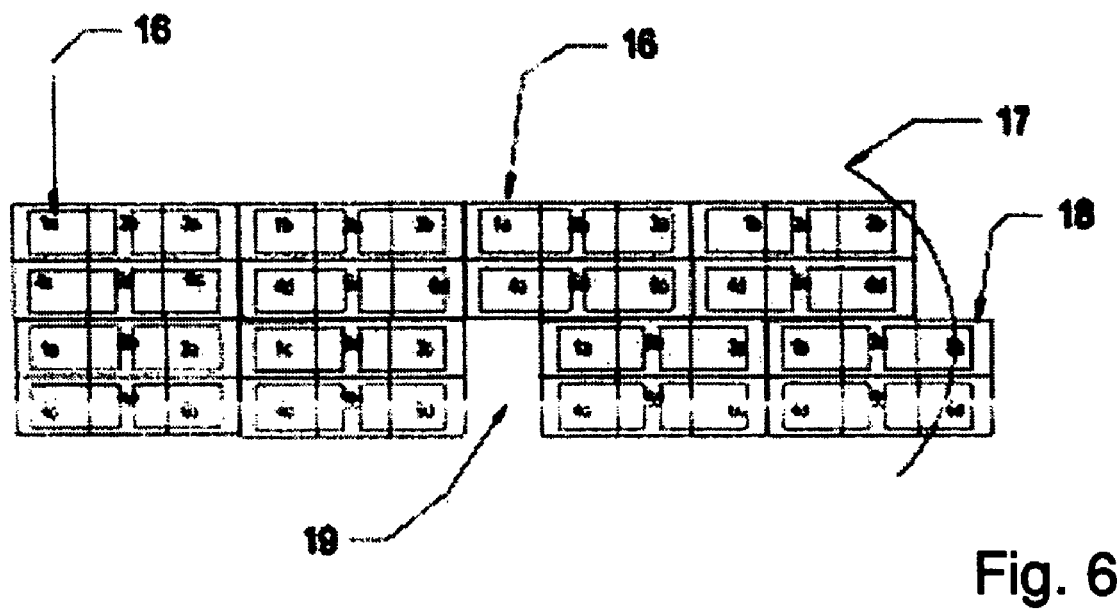
FIG. 6 shows an example of a combined index.

FIG. 6 now shows a section of a wafer having a wafer edge 17 and an edge area 18 which is also to be used in the analysis. The wafer also includes an offset 19 or a correspondingly structured control element.

In the combination of the two indices, the first segment obtains the index 1a. The first camera image comprises the image field segments 1a, 2b, 4c, 5d. The second camera image comprises the image field segments 3a, 1b, 6c, 4d etc. Thus the contents of the first and fourth images can be compared with each other, since they match both in the SAW and in the image index. Of course, both the individual image field segments of the first image can be compared with the corresponding image field segments of the fourth image, and groups of image field segments of the first image can be compared with those of the second image with the respective associations remaining identical.

When comparing the image field segments, it should be noted, however, that images having the same image contents must always be compared. Herein, "the same contents" means that the same structural elements are present in the individual images. A displacement of the SAWs with respect to each other, as it is used for an optimal utilization of the wafer surface, should be treated with the same approach. With the method according to the present invention, edge areas of wafers can be tested in the same way. A comparison operation is only carried out after the system has recorded three images with the same image contents. This means that in the present case about three images having the same image contents are recorded from the edge areas and they remain stored in the intermediate memory until a comparison operation can be carried out.

Figure 7:
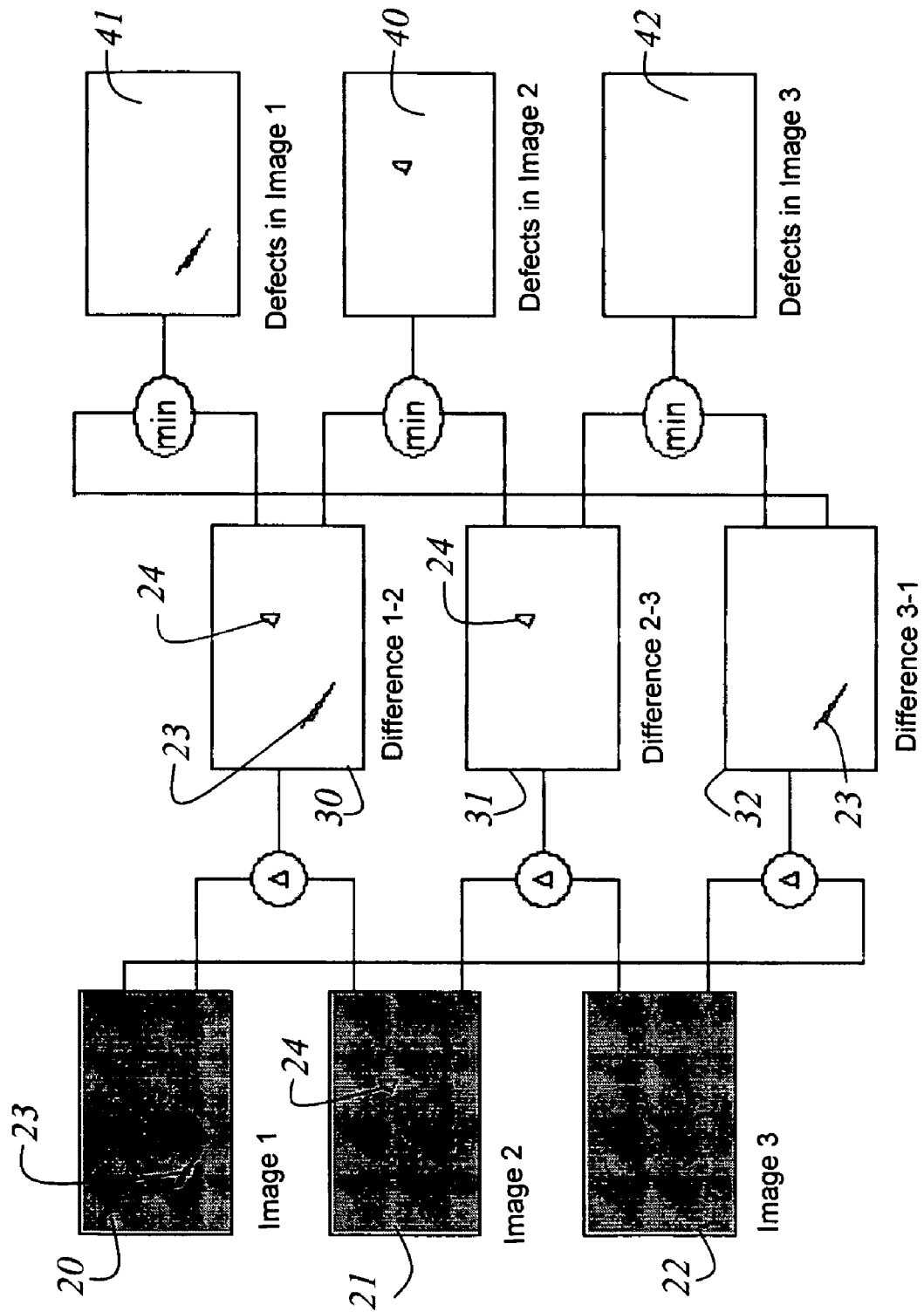
FIG. 7 shows a schematic sequence of the method according to the present invention.

FIG. 7 schematically shows an operating sequence of the method according to the present invention. According to the present method, the recorded individual images are randomly accessed. The described method implements a kind of "image cache", i.e. an intermediate memory area intermediately storing a variable number of recorded individual images and maintaining them for random access in the comparison operation. Herein, to begin with, three successively recorded individual images 20, 21 and 22 are compared, as soon as three fully comparable partner images have been recorded. The term "fully comparable partner images" means that the individual images to be compared have matching image contents due to the structured elements on the surface of disk-like object 1. The continued recording of individual images and their storage in the intermediate memory is carried out simultaneously with the comparison operation to be carried out.

The comparison of the recorded individual images 20, 21 and 22 is carried out in a process utilizing groups of three at any one time. This technique, using groups of three, also minimizes the alignment problems described below. By randomly accessing the recorded individual images it is also possible to analyze edge section images and also to take border zones on disk-like object 1 into account. Partner images can be relied upon to analyze these kinds of images, which have already been analyzed, or are still to be analyzed, in other groups of three. Moreover, the comparisons are not limited to a single scanning line. Also, after the comparison, false majority decisions are looked for and, when found, the images in question are regrouped in new groups of three and analyzed again. According to the method of the present invention a first difference 30 is formed of a first image 20 and a second image 21, further a second difference 31 is formed of a second image 21 and a third image 22, and a third difference 32 is formed of a third image 22 and first image 20. Since the individual images 20, 21 and 22 have matching image contents, what remains in difference images 30, 31 and 32 is only the distinctive features. In order to obtain an unequivocal allocation of the defects to their original images, a comparison operation must be carried out between difference images 30, 31 and 32. This comparison operation serves to compare the image contents of the third difference image 32 with the image contents of the first difference image 30. The result is a first comparison image 41 which actually reflects defect 23 included in the first individual image 20. In a second comparison operation, the first difference image 30 is compared with the second difference image 31 so that, as a result, a second comparison image 40 is obtained comprising the defect included in the second recorded individual image 21. In a third comparison operation, the second difference image 31 is compared to the third difference image 32 so that, as a result, a third comparison image 42 is obtained which does not comprise any defect. In the third recorded individual image 22, no defect is included, either. The first comparison image 41, the second comparison image 40 and the third comparison image 42 thus provide a defined judgment as to the presence of defects in the recorded individual images 20 to 22.

Before the three recorded individual images 20, 21 and 22 are compared with each other, they must be displaced with respect to each other with subpixel accuracy. First the present displacement of the three recorded individual images 20, 21 and 22 with respect to each other is measured with subpixel accuracy. From these data, an optimal displacement to be carried out for each of the recorded individual images 20, 21 and 22 is calculated which results in the three contents of the recorded individual images 20, 21 and 22 taking up the same position within their images with subpixel accuracy. The optimization is carried out separately for the x and y directions and consists in minimizing the amount of subpixel percentage of each displacement. The undesirable corruption of the images by subpixel displacement can thus be limited. It can be achieved that the subpixel percentage is no bigger than a third of a pixel in any direction in any of the displacements.

This method is not optimal, however, since it involves the three recorded individual images 20, 21 and 22 being displaced to differing degrees and therefore in soft focus to different extents. For this reason there is an additional, precisely measured, explicit soft-focussing which is carried out for each of the images, and in the x and y directions, to a different degree in order to extend the effect of soft-focussing in each case to a standard amount. The standard amount for the soft-focus effect in the x and y directions corresponds to the effect of the maximum possible subpixel displacement described in the present method, which is a third of a pixel. This also serves to solve the problem that different pairs of images have a differing degree of soft focus after their alignment with respect to each other. After the complete alignment, the soft focus corresponds to the same standard amount in all of the images of all groups of three of the recorded individual images 20, 21 & 22. Since the subpixel displacement is a convolution with a 2×1 or 2×2 convolution kernel (one direction and both directions simultaneously, respectively) and the explicit soft-focussing is a convolution with a 3×1 or 3×3 convolution kernel, respectively, for performance enhancement, it is a good idea to combine the two and to carry them out simultaneously in a good approximation by using a single 3×1 or 3×3 convolution.

After the alignment consisting of displacement and soft-focussing, all three differences can be created at once without further displacement. As can be seen from the diagram in FIG. 7, the image comparison and the allocation of the defects to their recorded individual images 20, 21 and 22 is already fully solvable within one group of three.

Figure 8:
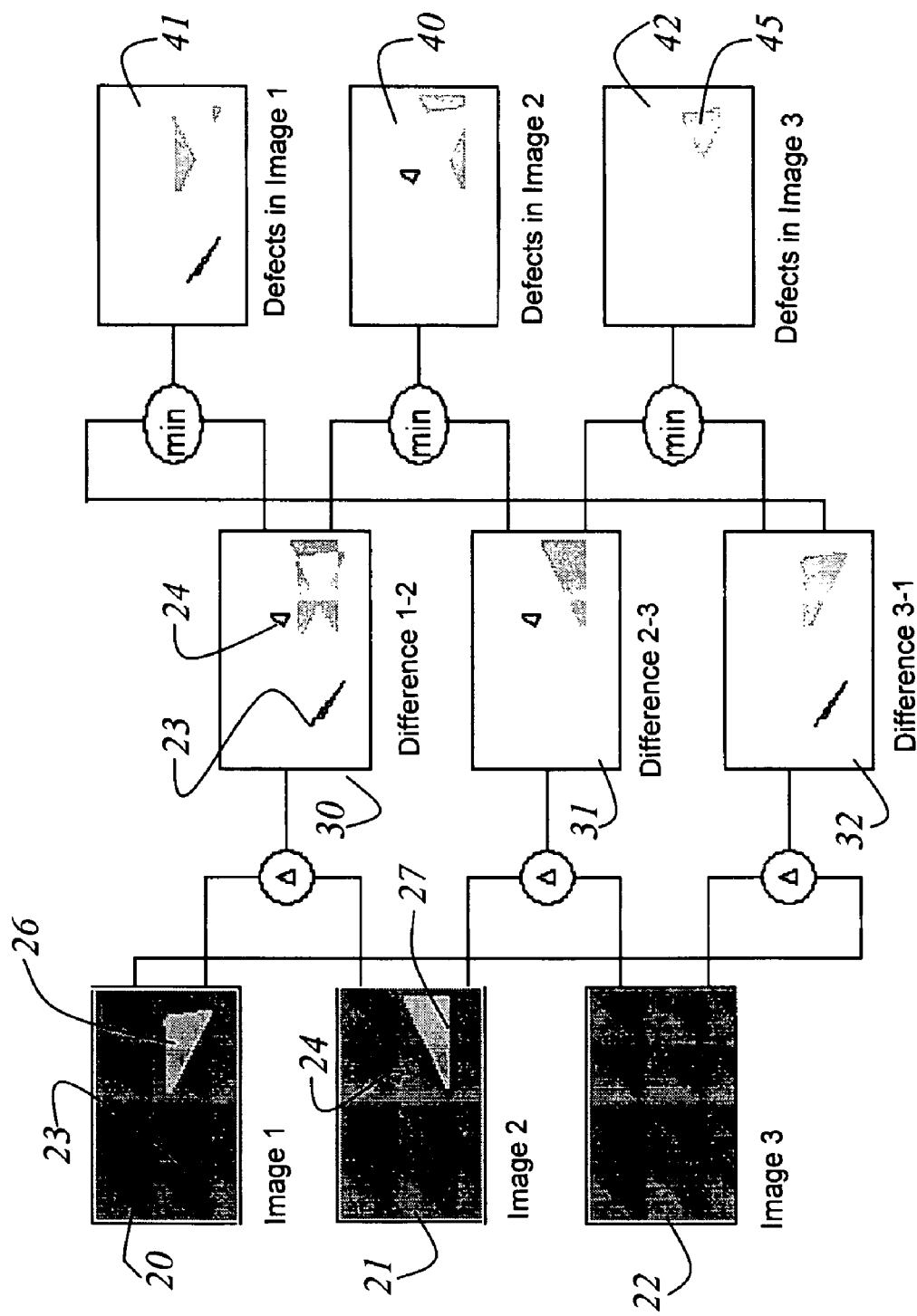
FIG. 8 shows a schematic sequence of the method according to the present invention wherein in part of the recorded images there are photoresist defects.

FIG. 8 shows the method according to the present invention in which, in spite of the use of groups of three recorded individual images 20, 21 and 22, errors in the allocation of the defects are still possible. If in two of the three comparison partner images, a defect is in exactly the same location, this defect will be seen as normal and the defect-free section in the third comparison partner image will be deemed defective. There is therefore a false majority decision. This situation, while rare, can still occur in particular with large photoresist defects. An example of this is illustrated in FIG. 8. In the first recorded individual image 20, apart from scratch 23, additionally a large first photoresist defect 26 is provided. In the second recorded individual image 21, apart from triangular defect 24, also a second large photoresist defect 27 is provided, which has a different position and orientation from the first large photoresist defect 26.

The overlapping area of the first photoresist defect 26 in the first individual image 20 and the second photoresist defect 27 in the second individual image 21 is detected as a match in both the first 41 and the second comparison image 40 in the same way, which thus excludes its detection as a defect.

On the other hand, the differences in shape between photoresist defect 26 and photoresist defect 27 are correctly indicated as defects in comparison images 40 and 41.

In comparison image 42 the overlapping area of the first photoresist defect 26 in the first individual image 20 and of the second photoresist defect 27 in the second individual image 21 appears as a smudge 45 indicating a defective region. In this case photoresist defects 26 and 27 in the first recorded individual image 20 and in the second recorded individual image 21 overruled, so to speak, the in fact defect-free individual image 22, resulting in a false majority decision.

Figure 9:
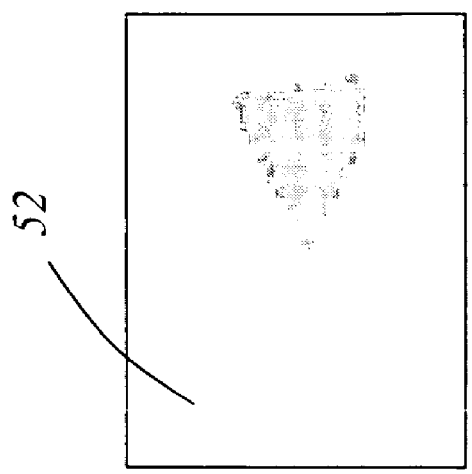
FIG. 9 schematically shows the result of the comparison operation from the image comparison carried out according to FIG. 8.
Figure 9:
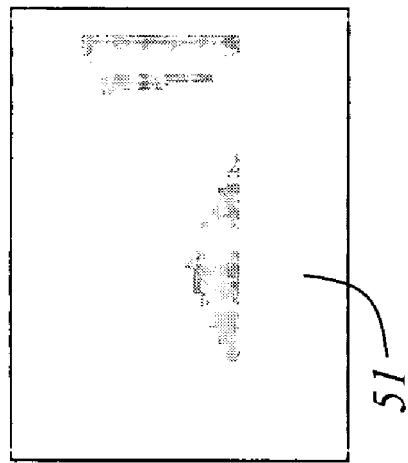
Figure 9:
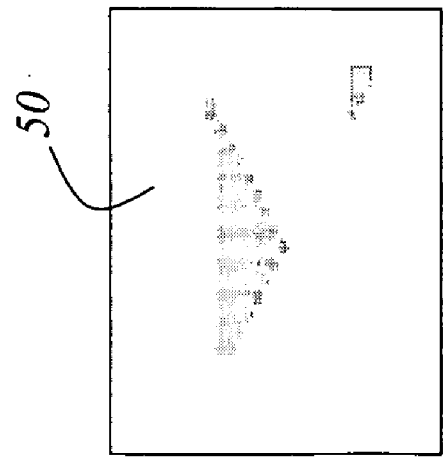

FIG. 9 shows the problematic situation of FIG. 8 in an enlarged view. After carrying out the defect detection and defect allocation it is determined whether there is a false majority decision. If this is indeed the case, the comparison partners in question will be compared with new, i.e. other partners, one more time in order to thus eliminate the equivocation in the allocation of the defects found.

It is possible, however, that no other suitable comparison partner can be found or that the same problematic situation arises with other comparison partners. It is therefore necessary to limit the number of further attempts to find a partner and if necessary to accept the unsatisfactory result of an unreliable defect allocation. FIG. 9 shows large defect 50 assigned to the first recorded individual image 20. FIG. 9 also shows large defect 51 assigned to the second recorded individual image 21. FIG. 9 further shows large defect 52 assigned to the third recorded individual image. As already described with reference to FIG. 8, the allocation of the third large defect 52 is based on a false majority decision. Here large defects 52 of the third comparison image 42 should in fact be assigned to both the first recorded individual image 20 and the second recorded individual image 22.

It is quite obvious that the problematic defective regions are characterized in that when they are superimposed they form a continuous overall area. Of course this only applies if the actual defect regions differ in form. However, precisely matching defects at exactly the same corresponding location in two images of different places on the wafer are a negligibly rare result, which is therefore not considered in any more detail.

Figure 10:
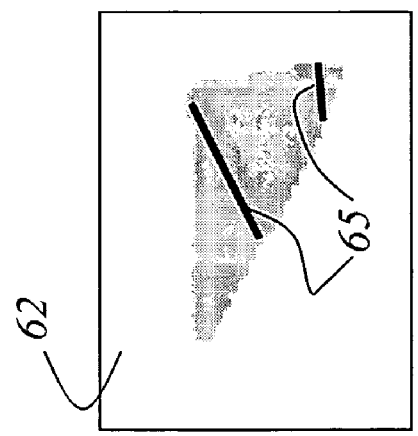
FIG. 10 is a schematic representation of an improved detection of defects in the images compared with each other.
Figure 10:
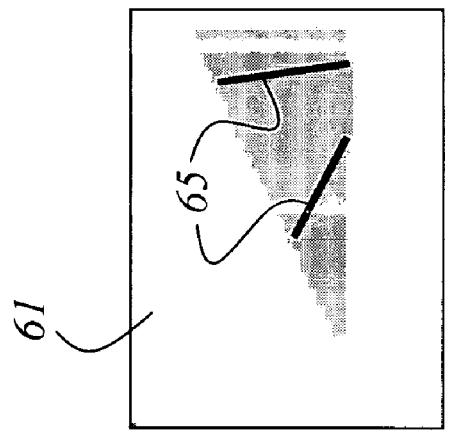
Figure 10:
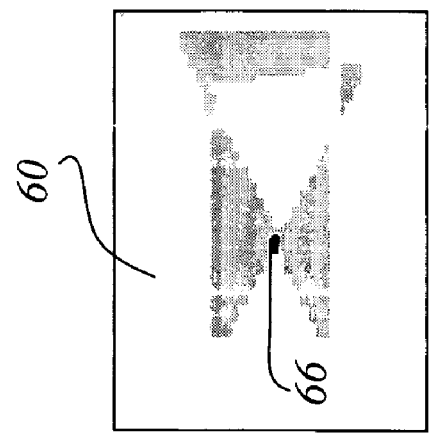

In FIG. 10 an approach is suggested which eliminates the erroneous allocation with large defects in the recorded individual images. In a first superimposed image 60 of the large defects of the recorded individual images 50 and 51, the border lines 66 are shown in dark representation. In a second superimposed image 61 of the defect images 51 and 52, the border lines 65 of the photoresist defects in the second recorded individual image 21 and the third recorded individual image 22 are also shown as dark lines. The border areas in the third superimposed image 62 of the defect images 52 and 50 are also indicated with dark border lines 65. The border lines in the second difference image 61 and in the third difference image 62 are easily discernible and stand out against the original noise. In the first difference image 61, the common border line between the large photoresist layers of the recorded individual images essentially only consists of one common point 66. Common point 66 cannot be differentiated, however, from the image noise with any reliable accuracy. Accordingly, in the method according to the present invention, common border lines having a certain minimum length are looked for in the associated defect regions of a group of three of the recorded individual images 20, 21 and 22. If such lines are found, the detection result for this group of three is deemed equivocal. It is then attempted to find new comparison partners for the members of this group of three. The unreliable detection results are only finally accepted if, at the end of a wafer, no new partners are possible.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of detecting defects in a plurality of images having essentially the same image contents, comprising the steps of:
   recording a plurality of individual images of a surface of a disk-like object;
   storing the individual images in an intermediate memory;
   carrying out a comparison operation once three fully comparable images having essentially the same image contents are present in the intermediate memory, wherein the stored individual images are randomly accessed and wherein the recording operation of the individual images is carried out in parallel to the comparison operation; in that a first difference is formed of the first and second recorded individual images, a second difference is formed of the second and third recorded individual images and a third difference is formed of the third and first recorded individual images, and in that by means of a comparison between the third difference and the first difference, by means of a comparison between the first difference and the second difference and by means of a comparison between the second difference and the third difference the presence of a defect in the recorded individual images is determined;

wherein the defects found in the individual images are tested as to the presence of false majority decisions and wherein, when a false majority decision is present, the detection is repeated with other comparison partners.

2. The method according to claim 1, wherein the random access to the recorded individual images also facilitates the analysis of edge section images and of exclusion zones on the disk-like object.

3. The method according to claim 2, wherein for the analysis of the individual images of edge section images and of exclusion zones, partner images are relied upon which have already been analyzed in other groups of three or which still have to be analyzed.

4. The method according to claim 1, wherein the comparison operation between the three recorded individual images is not limited to the recorded individual images of a single scanning line.

5. The method according to claim 1, wherein for an alignment of the three recorded individual images the present displacement of the three recorded individual images with respect to each other is first measured with subpixel accuracy and wherein from these data an optimal displacement to be carried out is calculated for each of the recorded individual images with the result that the three recorded individual images to be compared eventually have their image contents assume the same position within their image with subpixel accuracy.

* * * * *